(12) United States Patent
Avior

(10) Patent No.: US 8,579,973 B2
(45) Date of Patent: Nov. 12, 2013

(54) EUSTACHIAN TUBE DEVICE

(76) Inventor: Galit Avior, Cesarea (IL)

( * ) Notice: Subject to any disclaimer, the term of this patent is extended or adjusted under 35 U.S.C. 154(b) by 0 days.

(21) Appl. No.: 13/435,696

(22) Filed: Mar. 30, 2012

(65) Prior Publication Data

US 2012/0191030 A1     Jul. 26, 2012

Related U.S. Application Data

(63) Continuation of application No. 12/666,586, filed as application No. PCT/IL2008/000873 on Jun. 26, 2008, now Pat. No. 8,147,545.

(60) Provisional application No. 60/946,151, filed on Jun. 26, 2007.

(51) Int. Cl.
    *A61F 2/18*        (2006.01)
    *A61F 11/00*     (2006.01)

(52) U.S. Cl.
    USPC ............................... 623/10; 606/108; 606/109

(58) Field of Classification Search
    CPC ........................................................ A61F 2/18
    USPC ..................................... 623/10; 606/108, 109
    See application file for complete search history.

(56) References Cited

U.S. PATENT DOCUMENTS

| | | |
|---|---|---|
| 3,916,873 A | 11/1975 | Wasserman |
| 4,037,604 A | 7/1977 | Newkirk |
| 4,168,697 A | 9/1979 | Cantekin |
| 4,568,337 A | 2/1986 | Treharne, III et al. |
| 4,808,171 A | 2/1989 | Berger |
| 5,350,580 A | 9/1994 | Muchow et al. |
| 5,746,725 A | 5/1998 | Shalon et al. |
| 6,245,077 B1 | 6/2001 | East et al. |
| 6,578,581 B1 | 6/2003 | Khalsa |
| 6,589,286 B1 | 7/2003 | Litner |
| 2003/0191527 A1 | 10/2003 | Shaknovich |
| 2007/0010868 A1* | 1/2007 | Ferren et al. ................. 623/1.15 |
| 2008/0294255 A1 | 11/2008 | Gonzales |

OTHER PUBLICATIONS

International Search Report of Application No. PCT/IL2008/000873 mailed on Jan. 21, 2009.

* cited by examiner

*Primary Examiner* — Jason-Dennis Stewart
(74) *Attorney, Agent, or Firm* — Heslin Rothenberg Farley & Mesiti P.C.

(57) ABSTRACT

A device stenting the Eustachian tube is inserted through the nasopharynx and provides enhanced ventilation and drainage to the middle ear. Also provided is a method for inserting the device into the Eustachian tube and through the isthmus of a human subject.

10 Claims, 3 Drawing Sheets scale 20:1

(ALL DIMENSIONS ARE IN MM.)

scale 20:1
(ALL DIMENSIONS ARE IN MM.)

EUSTACHIAN TUBE DEVICE

CROSS-REFERENCE TO RELATED APPLICATIONS

This application is a continuation of application Ser. No. 12/666,586 filed on Dec. 23, 2009 which is a national phase filing of International Application No. PCT/IL08/00873 filed on Jun. 26, 2008, and published in English as WO2009001358 on Dec. 31, 2008 which claims priority of U.S. application 60/946,151 filed on Jun. 26, 2007, the entire contents of all of these applications being hereby incorporated by reference herein.

FIELD OF THE INVENTION

The invention provides stent devices for adequate ventilation and drainage for normal middle ear function.

BACKGROUND OF THE INVENTION

Adequate ventilation and drainage is essential for normal middle ear function. The Eustachian tube is purported to function in middle ear ventilation, drainage, and protection. Chronic Eustachian tube dysfunction has been implicated in the pathogenesis of many otologic disorders and is thought to be a principal cause of surgical failures. Patients with chronic middle ear disease have often been shown to have a mechanical narrowing of the Eustachian tube, usually at the isthmus (junction of the bony and cartilaginous portions), other causes for ET dysfunction are functional disorders of the cartilaginous part. Narrowing of the isthmus alone was demonstrated to be an insufficient cause of otitis media. Increasing evidence was found that allergic disease and reflux may be two of the most important contributors of tubal inflammation causing otitis media with effusion.

The tube is ordinarily closed in the resting position and dilates to the open position typically with swallows, yawns, and with other voluntary or involuntary efforts. Tubal opening typically lasts less than one-half second. Closure of the tube is maintained by a valve-like function of the opposing mucosal surfaces, submucosal tissue, fat, muscle, and cartilage. The valve measures approximately 5 mm in length and lies within the cartilaginous portion of the ET located about 10 mm distal into the tube from the nasopharyngeal orifice's posterior cushion or torus tubarius. The patulous ET has been defined as an abnormal patency that results in autophony A common problem resulting from Eustachian tube dysfunction is Otitis Media with Effusion (OME) or the presence of fluid in the middle ear with no signs or symptoms of acute ear infection. Persistent middle ear fluid from OME results in decreased mobility of the tympanic membrane and serves as a barrier to sound conduction. OME may occur spontaneously because of poor Eustachian tube function or as a response following Acute Otitis Media. This usually occurs in infants and children aged 1-6 y due to anatomical difference and physiological changes of the Eustachian tube. At birth the tube is horizontal and 17 to 18 mm long. It grows to be at an incline of 45 degrees and reaches the length of 35 mm in adulthood. Due to its' relatively horizontal position in childhood and because it is shorter, infants are more likely to suffer from Eustachian tube dysfunction.

Most surgical procedures performed at this time involve bypassing the blocked Eustachian tube by implantation of a surgical prosthesis, usually in the tympanic membrane (ear drum), for ventilation of the middle ear cavity via the external ear canal. Tympanostomy tubes are recommended for initial surgery. Often, however, complications are encountered with such tubes. The main complications associated with tympanostomy tubes insertion are divided to early and late. Early complications: persistent otorrehea 10-26%, blockage of the tube 0-9%, early extrusion, hearing loss. Late complications: persistent perforation after tube extrusion 3%. Scarring of the tympanic membrane, atrophic membrane 21-28%, granuloma 5-40%, Tympanosclerosis 40-65%, cholesteatoma 1%.

SUMMARY OF THE INVENTION

In one embodiment, the present invention provides a device for insertion into a Eustachian tube in a subject providing pressure controlled ventilation, and enhanced drainage, or a combination thereof to a middle ear of a subject, comprising a shell, wherein the shell comprises a proximal end, a distal end, wherein the device occupies at least a portion of the proximal portion of said Eustachian tube of a subject.

In another embodiment, the present invention further provides a method for placing a device within an Eustachian tube of a subject, comprising: (a) loading said device onto an insertion apparatus, wherein said device comprises a shell, wherein said shell comprises a proximal end, a distal end wherein, said device occupies at least a portion of the proximal end of said Eustachian tube of a subject. (b) inserting said device using said insertion apparatus through a nostril or mouth of said subject into said Eustachian tube; and (c) releasing said device from the apparatus in said Eustachian tube.

DETAILED DESCRIPTION OF THE INVENTION

Figure 1:
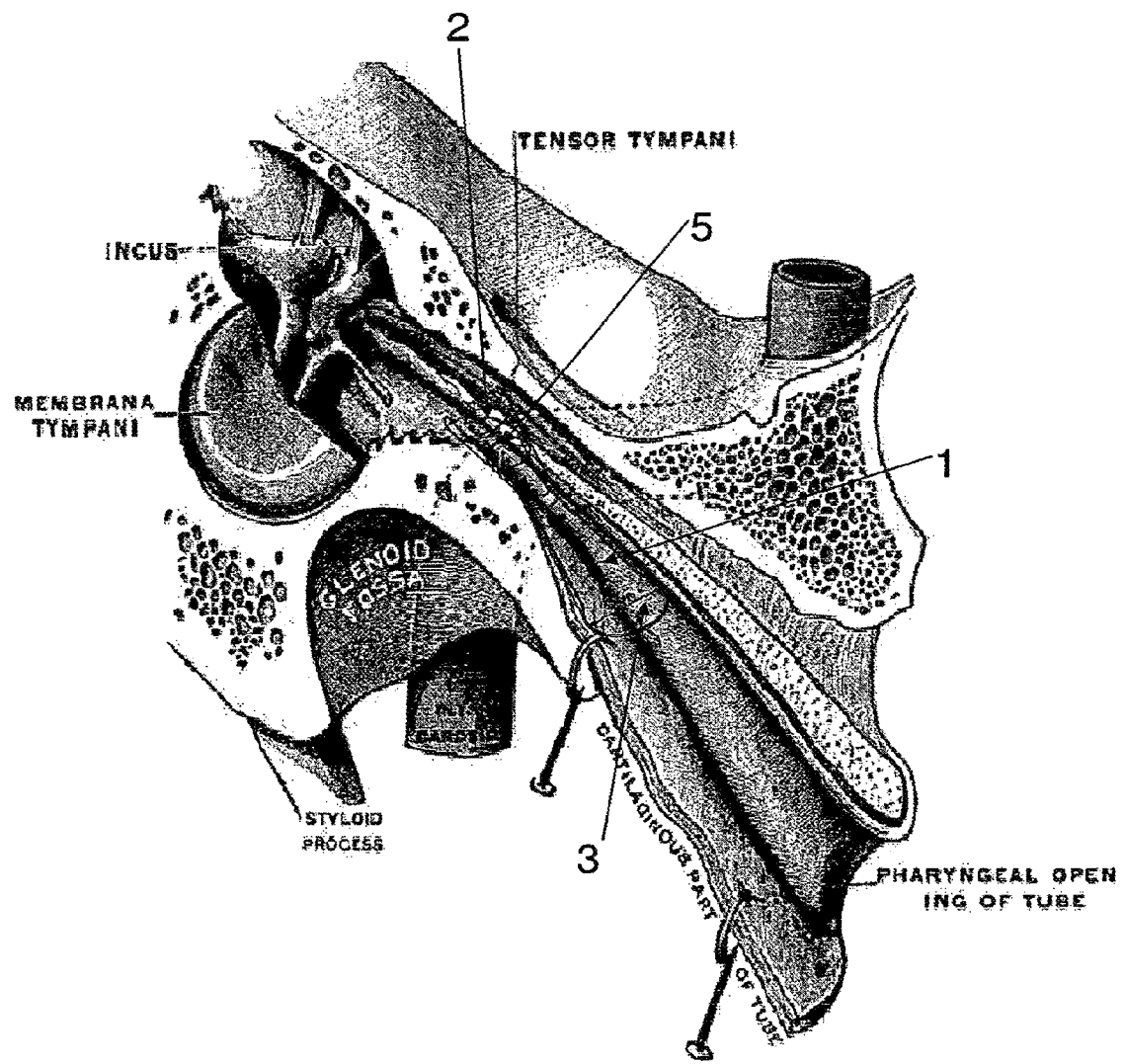
FIG. 1. is schematic drawing of the Device-Stent placed in the Eustachian tube in accordance with an embodiment of the invention. The proximal end (3) occupies part of the proximal portion of the Eustachian tube and the distal end (4) occupies part of the distal portion of the Eustachian tube.

In one embodiment, the invention provides a device for insertion into a Eustachian tube in a subject providing pressure controlled ventilation, and enhanced drainage, or a combination thereof to a middle ear of a subject, comprising a shell, wherein the shell comprises a proximal end, a distal end, wherein the device occupies at least a portion of the proximal portion of the Eustachian tube of a subject. In another embodiment, the device of occupis only said Eustachian tube. In another embodiment, the device proximal and/or distal ends are placed within the Eustachian tube. In another embodiment, the device proximal and/or distal ends remain placed within the Eustachian tube. In another embodiment, the device proximal and/or distal ends anchor the device to the Eustachian tube. In another embodiment, the device does not exceed the boundaries of the Eustachian tube. In another embodiment, the shell is a coaxial shell. In another embodiment, the device is located within the proximal portion of the ET and does not extend beyond the proximal portion of the ET. In another embodiment, the device does not exceed the boundaries of the Eustachian tube. In another embodiment, the proximal portion of the ET is located between the proximal end of ET and the proximal end of the isthmus.

In another embodiment, the present invention provides a device for insertion through the Eustachian tube providing enhanced ventilation, drainage, or a combination thereof to a middle ear of a subject, comprising a shell, wherein the shell comprises a proximal end, a distal end, and an intermediate portion, wherein the proximal end and the distal end have a larger cross-section area than the intermediate portion cross-section area, wherein the intermediate portion fits within an isthmus in a subject.

In another embodiment, the invention further provides a method for inserting a device into an Eustachian tube (ET) and through the nasopharynx into the ET of a subject, comprising: (a) loading the device onto an insertion apparatus, wherein the device comprises a shell comprising a proximal end, a distal end, and an intermediate portion, wherein the proximal and the distal ends have a larger cross-section area than the intermediate portion cross-section area, wherein the intermediate portion fits within the isthmus that is located in the Eustachian tube in a subject; (b) inserting the device using an insertion apparatus through a nostril or mouth of a subject into the isthmus; and (c) releasing the device from the apparatus and into the isthmus.

In another embodiment, the proximal end cross-section area is larger than the distal end cross-section area. In another embodiment, the device further comprises an intermediate portion. In another embodiment, the proximal end and the distal end have a larger cross-section area than the intermediate portion cross-section area, wherein said intermediate portion fits within said Eustachian tube in said subject In another embodiment, the invention provides a device for insertion into a Eustachian tube in a subject providing pressure controlled ventilation, and enhanced drainage, or a combination thereof to a middle ear of a subject, comprising a shell, wherein the shell comprises a proximal end, a distal end, and an intermediate portion, wherein the proximal end and the distal end have a larger cross-section area than the intermediate portion cross-section area, wherein the intermediate portion fits within the Eustachian tube in a subject. In another embodiment, the device is inserted through the isthmus.

In another embodiment, the invention provides a device for insertion through the isthmus providing pressure control ventilation, and enhanced ventilation, drainage, or a combination thereof to a middle ear of a subject, comprising a shell (FIGS. 2 and 3), wherein the shell comprises a proximal end (3), a distal end (4), and an intermediate portion (5), wherein the proximal end and the distal end have a larger cross-section area than the intermediate portion cross-section area, wherein the intermediate portion fits within an isthmus in a subject. In another embodiment, the intermediate portion is compressible and can extend along the isthmus. In another embodiment, the device is packed in a compressed form and can extend along the isthmus. In another embodiment, the device is packed in a compressed form and can extend along the ET. In another embodiment, the shell is compressible and can extend along the isthmus.

In one embodiment, the invention provides a device for insertion through the isthmus providing enhanced ventilation, drainage, or a combination thereof to a middle ear of a subject, comprising a coaxial shell, wherein the shell comprises a proximal end (3), a distal end (4), and an intermediate portion (5), wherein the proximal end and the distal end have a larger cross-section area than the intermediate portion cross-section area, wherein the intermediate portion fits within an isthmus in a subject. In another embodiment, the intermediate portion is compressible and can extend along the isthmus. In another embodiment, the shell is compressible and can extend along the isthmus.

In another embodiment, the device extends along the Eustachian tube. In another embodiment, the device extends along the proximal portion of the Eustachian tube. In another embodiment, the device location is confined to the Eustachian tube. In another embodiment, the device location is confined to the proximal part of the Eustachian tube (proximal to the isthmus).

In another embodiment, the invention provides a device for stenting the Eustachian tube providing pressure controlled ventilation or enhanced drainage, or a combination thereof to a middle ear of a subject comprising a proximal end occupying the proximal portion of the Eustachian tube and a distal end occupying the narrowed proximal portions of the Eustachian tube. In another embodiment, the invention provides a device for stenting the proximal portion of the Eustachian tube providing pressure controlled ventilation or enhanced drainage, or a combination thereof to a middle ear of a subject, wherein the device comprises a distal end occupying the narrowed proximal portions of the Eustachian tube. In another embodiment, the invention provides a device for stenting the proximal portion of the Eustachian tube providing pressure controlled ventilation or enhanced drainage, or a combination thereof to a middle ear of a subject, wherein the device comprises a distal end occupying a location in proximity to the isthmus. In another embodiment, the invention provides a device for stenting the proximal portion of the Eustachian tube providing pressure controlled ventilation or enhanced drainage, or a combination thereof to a middle ear of a subject comprising a cone, a funnel, or a triangular shape wherein the narrow portion of the cone, funnel, or triangular shape is placed in proximity to the isthmus. In another embodiment, the invention provides a device for stenting the proximal portion of the Eustachian tube providing pressure controlled ventilation or enhanced drainage, or a combination thereof to a middle ear of a subject, wherein the device comprises a cone, a funnel, or a triangular shape wherein the narrow portion of the cone, funnel, or triangular shape is the distal end of the device. In another embodiment, the invention provides a device for stenting the proximal portion of the Eustachian tube providing pressure controlled ventilation or enhanced drainage, or a combination thereof to a middle ear of a subject comprising a cone, a funnel, or a triangular shape wherein the wide portion of the cone, funnel, or triangular shape is the proximal end of the device. In another embodiment, the invention provides a device for stenting the proximal portion of the Eustachian tube providing pressure controlled ventilation or enhanced drainage, or a combination thereof to a middle ear of a subject comprising a cone, a funnel, or a triangular shape wherein the proximal end is an opening. In another embodiment, the invention provides a device for stenting the proximal portion of the Eustachian tube providing pressure controlled ventilation or enhanced drainage, or a combination thereof to a middle ear of a subject comprising a cone, a funnel, or a triangular shape wherein the distal end is an opening. In another embodiment, the invention provides a device comprising a pressure actuated valve for stenting the proximal portion of the Eustachian tube providing pressure controlled ventilation or enhanced drainage, or a combination thereof to a middle ear of a subject comprising a cone, a funnel, or a triangular shape, wherein the narrow portion of the cone, funnel, or triangular shape is the distal end of the device.

In another embodiment, the invention provides a device for stenting the Eustachian tube providing pressure controlled ventilation or enhanced drainage, or a combination thereof to a middle ear of a subject. In another embodiment, the invention provides a stenting device to be placed through the isthmus providing pressure controlled ventilation or enhanced drainage, or a combination thereof to a middle ear of a subject. In another embodiment, the intermediate portion of the device is placed within the isthmus providing pressure controlled, drainage, or a combination thereof to a middle ear of a subject. In another embodiment, the intermediate portion of the device is placed within the isthmus and extends proximally and distally over the isthmus In another embodiment, the extensions of the intermediate portion over the end of the isthmus result in a proximal end and a distal end of the device. In another embodiment, the extensions of the intermediate portion beyond the isthmus, and within the Eustachian tube.

In another embodiment, the intermediate portion of the device is designed to be placed within the narrow isthmus while the proximal end and a distal end are situated proximally and distally to the isthmus within the wider Eustachian tube. In another embodiment, the intermediate portion of the device is narrow while the proximal end and the distal end of the device are wider. In another embodiment, the proximal end and the distal end of the device protrude outside of the isthmus into the Eustachian tube. In another embodiment, the proximal end cross-section area is larger than the distal end cross-section area. In another embodiment, the distal end cross-section area is larger than any cross-section are within the intermediate portion. In another embodiment, the proximal end and the distal end are openings. In another embodiment, an interconnecting space is located between the proximal end and the distal end. In another embodiment, the openings have narrower diameter than both the proximal end diameter and the distal end diameter. In another embodiment, the proximal opening and the distal opening have the same diameter. In another embodiment, the proximal opening and the distal opening have a different diameter. In another embodiment, the proximal end and the distal end are interconnected by a tube.

In another embodiment, the proximal end cross-section area is at least 1.2 times larger than the distal end cross-section area. In another embodiment, the proximal end cross-section area is at least 1.4 times larger than the distal end cross-section area. In another embodiment, the proximal end cross-section area is at least 1.5 times larger than the distal end cross-section area. In another embodiment, the proximal end cross-section area is at least 1.8 times larger than the distal end cross-section area. In another embodiment, the proximal end cross-section area is at least 2 times larger than the distal end cross-section area. In another embodiment, the proximal end cross-section area is at least 2.5 times larger than the distal end cross-section area. In another embodiment, the proximal end cross-section area is at least 3 times larger than the distal end cross-section area. In another embodiment, the proximal end cross-section area is at least 4 times larger than the distal end cross-section area. In another embodiment, the proximal end cross-section area is at least 5 times larger than the distal end cross-section area. In another embodiment, the proximal end cross-section area is at least 6 times larger than the distal end cross-section area. In another embodiment, the proximal end cross-section area is at least 8 times larger than the distal end cross-section area. In another embodiment, the proximal end cross-section area is at least 10 times larger than the distal end cross-section area.

In another embodiment, the device diameter is between 0.3-6 mm. In another embodiment, the device diameter is between 0.5-4 mm. In another embodiment, the device diameter is between 1-6 mm. In another embodiment, the device diameter is between 1-5 mm. In another embodiment, the device diameter is between 2-5 mm. In another embodiment, the device diameter is between 2-4 mm. In another embodiment, the device diameter is between 3-6 mm. In another embodiment, the device diameter is between 0.3-3 mm.

In another embodiment, the device width regardless of its shape (i.e. tube, triangular, etc.) is between 0.3-6 mm. In another embodiment, the device width regardless of its shape (i.e. tube, triangular, etc.) is between 1-6 mm. In another embodiment, the device width regardless of its shape (i.e. tube, triangular, etc.) is between 0.5-5 mm. In another embodiment, the device width regardless of its shape (i.e. tube, triangular, etc.) is between 1-5 mm. In another embodiment, the device width regardless of its shape (i.e. tube, triangular, etc.) is between 0.3-4 mm. In another embodiment, the device width regardless of its shape (i.e. tube, triangular, etc.) is between 3-6 mm. In another embodiment, the device width regardless of its shape (i.e. tube, triangular, etc.) is between 0.3-3 mm. In another embodiment, the device width regardless of its shape (i.e. tube, triangular, etc.) is between 0.5-4 mm.

In another embodiment, the distal end cross-section area is at least 1.2 times larger than the largest cross-section area situated within the intermediate portion. In another embodiment, the distal end cross-section area is at least 1.5 times larger than the largest cross-section area situated within the intermediate portion. In another embodiment, the distal end cross-section area is at least 1.8 times larger than the largest cross-section area situated within the intermediate portion. In another embodiment, the distal end cross-section area is at least 2 times larger than the largest cross-section area situated within the intermediate portion. In another embodiment, the distal end cross-section area is at least 3 times larger than the largest cross-section area situated within the intermediate portion. In another embodiment, the distal end cross-section area is at least 4 times larger than the largest cross-section area situated within the intermediate portion. In another embodiment, the distal end cross-section area is at least 5 times larger than the largest cross-section area situated within the intermediate portion.

In another embodiment, the proximal end cross-section area is at least 1.2 times larger than the largest cross-section area situated within the intermediate portion. In another embodiment, the proximal end cross-section area is at least 1.5 times larger than the largest cross-section area situated within the intermediate portion. In another embodiment, the proximal end cross-section area is at least 1.8 times larger than the largest cross-section area situated within the intermediate portion. In another embodiment, the proximal end cross-section area is at least 2 times larger than the largest cross-section area situated within the intermediate portion. In another embodiment, the proximal end cross-section area is at least 3 times larger than the largest cross-section area situated within the intermediate portion. In another embodiment, the proximal end cross-section area is at least 4 times larger than the largest cross-section area situated within the intermediate portion. In another embodiment, the proximal end cross-section area is at least 5 times larger than the largest cross-section area situated within the intermediate portion.

In another embodiment, the shell is a coaxial shell. In another embodiment, the shell is continuous. In another embodiment, the shell made of a single piece of material. In another embodiment, the shell is not continuous. In another embodiment, the shell. In another embodiment, the shell comprises an array of spaces. In another embodiment, the term "array" refers to an arrangement of a discontinuos shell or spaces within the shell. In another embodiment, the array of this invention comprises spaces positioned on the array so as to form any desired geometrical shape including a circle, square, rectangle, triangle, polygons or other, as will be understood by one skilled in the art and will be so formed to suit a desired application. In another embodiment, a square arrangement of spaces in rows and columns, as in a matrix is being used. In another embodiment, positioning on the array with a particular pattern is desired, for example, spaces of varying geometries are positioned within a pattern. In another embodiment, a space positioning in the array is a function of the material applied to the shell. In another embodiment, the device may comprise more than one array. In another embodiment, the arrays may be arranged perpendicular with respect to each other, or in another embodiment, in parallel. In another embodiment, arrays might radiate outward from a single point, as spikes on a wheel.

In another embodiment, the shell is a spiral. In another embodiment, the shell is a coil. In another embodiment, the shell is a network of coils. In another embodiment, the shell is a spring.

In another embodiment, the shell is compressible. In another embodiment, the shell is extendable. In another embodiment, the shell is stretchable. In another embodiment, the shell is elastic. In another embodiment, the shell comprises rigid or semi rigid portions and elastic portions. In another embodiment, the intermediate portion is compressible and can extend along the isthmus. In another embodiment, the intermediate portion is compressible and can extend along the Eustachian tube.

In another embodiment, the device is an implantable device that is positioned within an anatomical cavity of the isthmus. In another embodiment, the device is an implantable device that is positioned within the anatomical cavity of the Eustachian tube to deliver a diagnostic to the Eustachian tube, tissues located adjacent to, or near the implanted device. In another embodiment, the device is an implantable device that is positioned within the anatomical cavity of the isthmus to deliver a diagnostic to the isthmus, tissues located adjacent to, or near the implanted device. In another embodiment, the device is an implantable device that is positioned within the Eustachian tube to support the Eustachian tube as an open passage. In another embodiment, the device is an implantable device that is positioned within the proximal portions of the Eustachian tube (proximal to the isthmus) to support the Eustachian tube as an open passage. In another embodiment, the device is an implantable device that is positioned within an anatomical cavity of the isthmus to support the isthmus as an open passage. In another embodiment, the device is an implantable device that is positioned within an anatomical cavity of the isthmus to support the Eustachian tube as an open passage.

In another embodiment, the shell is desirably compressive by any construction (e.g., a single tube element with ends that allow some compression. In another embodiment, the intermediate portion is a hollow tubular body. In another embodiment, the dimensions of the device can be varied in keeping with the variable dimensions of the human adult and pediatric Eustachian tubes. In another embodiment, the overall length of the device is about 15 to 40 mm. In another embodiment, the overall length of the device is about 20 to 30 mm. In another embodiment, the overall length of the device is about 22 to 26 mm. In another embodiment, the outside diameter of the proximal end is about 2 to 12 mm. In another embodiment, the outside diameter of the proximal end is about 4 to 10 mm. In another embodiment, the outside diameter of the proximal end is about 6 to 12 mm. In another embodiment, the outside diameter of the proximal end is about 6 to 10 mm. In another embodiment, the outside diameter of the distal end is about 2 to 8 mm. In another embodiment, the outside diameter of the distal end is about 3 to 7 mm. In another embodiment, the outside diameter of the distal end is about 3 to 6 mm. In another embodiment, the outside diameter of the distal end is about 3 to 5 mm. In another embodiment, the outside diameter of the distal end is about 4 to 5 mm.

In another embodiment, the device is 20 mm to 50 mm long. In another embodiment, the device is 30 mm to 50 mm long. In another embodiment, the device is 30 mm to 40 mm long. In another embodiment, the device is 31 mm to 38 mm long. In another embodiment, the device is 4 mm to 10 mm long. In another embodiment, the device is 4 mm to 50 mm long. In another embodiment, the device is 10 mm to 20 mm long. In another embodiment, the device is 15 mm to 30 mm long. In another embodiment, the device has an inverted S-shape.

In another embodiment, the device is comprised of a biocompatible material. In another embodiment, the device is comprised of a combination of biocompatible materials. In another embodiment, the device is comprised of a biocompatible material that provides the necessary physical properties for the device of the invention. In another embodiment, the device is comprised of a polymeric material (both natural and synthetic), a polymeric fiber, a ceramic material, a composite material, a metal, a metal oxide, and combinations thereof. In another embodiment, the device is comprised of amylose and amylopectin derivatives, polyamides, polyvinyl alcohol, polyvinyl acetals, polyvinylpyrrolidone, polyacrylates, epoxy resins, and polyurethanes (mixtures thereof, blends with other ingredients, or copolymers thereof) and combinations thereof.

In another embodiment, the device is coated. In another embodiment, the device is coated with a polymer or coating composition. In another embodiment, the device is coated with hyaluronic acid. In another embodiment, the device is coated with Perylenem™. In another embodiment, the device is coated with heparin. In another embodiment, the device is coated with a lubricant. In another embodiment, the device is coated with a thrombo-prevention compound. In another embodiment, the device is coated with an anti-bacterial compound. In another embodiment, the device is coated with an anti-inflammatory compound. In another embodiment, the device is cross-linked or bound to a drug by gamma irradiation, chemical binding (as with binder or crosslinking molecules such as N-hydroxysuccinimide), or any other method. In another embodiment, the device is capable of the controlled release of a drug such as a surfactant, lubricant, antibiotic, anti-acid, antifungal agent, anti-inflammatant, or the like, which has been shown to decrease the end pressure of the Eustachian tube.

In another embodiment, the device is formed in part or in whole from a number of materials. In another embodiment, the materials are typically selected so as to ensure optimal device performance given the particular construction and/or geometry of the device. In another embodiment, the materials are tailored to the environment conditions to which the device may be exposed. In another embodiment, the environmental conditions of the Eustachian tube may vary according to a number of factors, e.g., the particular temperature of the animal whose Eustachian is to receive the device, whether the Eustachian tube is healthy or diseased, whether pus or other bodily fluids are present, edema of the mucosa, absent of the fat pad, etc.

In another embodiment, the device is substantially uniform in composition. In another embodiment, the device comprises of a plurality of regions that form an integrated whole. In another embodiment, the device is comprised of an interior region and a peripheral region, wherein the regions exhibit different compositions. In another embodiment, the peripheral region is formed from a biocompatible material. In another embodiment, the microstructure of the materials used with the invention is controlled in order to produce a device of controlled mechanical properties (e.g., tensile strength, elasticity). In another embodiment, the material is typically synthetic or man-made. In another embodiment, naturally occurring composition are used. In another embodiment, biocompatibility requires a material purity of a pharmaceutically acceptable grade.

In another embodiment, the material is a hydrophilic polymer. In another embodiment, the material hydrophilic polymers include polyethylene glycol, polyoxyethylene, polymethylene glycol, polytrimethylene glycols, polycinylpyrrolidones, and derivatives thereof. In another embodiment, the polymers are linear or multiply branched. In another embodiment, the material is polyethylene glycol (PEG) containing compound. In another embodiment, the material is a polyvinyl alcohol, polyacrylic acid, polyglycolic acid, polydioxanone. In another embodiment, the material is a biodegradable material such as polyesters of an α-hydroxy acids, lactic acid, glycolic acid, lactic esters, caprolactone, polyether-polyester combinations especially of polyethylene glycol (PEG) and aliphatic polyesters like poly (lactic acid), poly (glycolic acid) and poly (caprolactone), either as a blend or as a copolymer, in order to increase the hydrophilicity and degradation rate. In another embodiment, the material is a biodegradable polyanhydrides or polyorthoesters having labile backbone linkages.

In another embodiment, the material is a polysaccharide. In another embodiment, the material is hyaluronic acid. In another embodiment, the material is cyclodextrin. In another embodiment, the material is hydroxymethylcellulose. In another embodiment, the material is cellulose ether. In another embodiment, the material is a glycan. In another embodiment, the material is a collagen and other collagenic (collagen-like) materials In another embodiment, the device is used in conjunction with pharmaceutical technologies known in the art. In another embodiment, the shell includes a pharmacologically active constituent. In another embodiment, a pharmacologically active constituent is bound to the device member or may be eludable. In another embodiment, such pharmacologically active constituents may promote post-operative healing and may include, for example, antibiotics, antifungal agent, anti-inflammatory, or the like. In another embodiment, the biocompatible material may be free from any pharmacologically active constituents.

In another embodiment, the device comprises a pharmaceutical substance that treats or prevents a microbial infection, the substance delivered may comprise pharmaceutically acceptable salt or dosage form of an antimicrobial agent (e.g., antibiotic, antiviral, antiparacytic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc.

In another embodiment, the device comprises acyclovir, amantadine, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform); non-pathogenic or "friendly" microbes that cause the production of hydrogen peroxide or other substances that kill or inhibit the growth of pathogenic microbes (e.g., lactobacillus); antimicrobial proteins or peptides, or any combination thereof In another embodiment, the device comprises a pharmaceutical composition that treats or prevents inflammation; the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal administration may be used, such as beclomethasone (Vancenase.®. or Beconase.®.), flunisolide (Nasalide.®.), fluticasone proprionate (Flonase.®.), triamcinolone acetonide (Nasacort.®.), budesonide (Rhinocort Aqua.®.), loterednol etabonate (Locort) and mometasone (Nasonex.®.). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide), or any combination thereof.

In another embodiment, the device comprises a pharmaceutical composition that treats or prevents an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors, or any combination thereof.

In another embodiment, the device comprises a pharmaceutical composition that shrinks mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

In another embodiment, the device comprises a pharmaceutical composition that facilitates the flow of mucous, the substances delivered in this invention may include various mucolytics or other agents that modify the viscosity or consistency of mucous or mucoid secretions, including but not limited to acetylcysteine (Mucomyst.™., Mucosil.™.) and guaifenesin.

In another embodiment, the device comprises a pharmaceutical composition that comprises any combination of an active pharmaceutical ingredient as described herein.

In another embodiment, the device is produced by pouring a sterile solution of a precursor member material onto a sterile mold. In another embodiment, the mold is composed of a biocompatible material. In another embodiment, the mold is composed of stainless steel. In another embodiment, the mold is composed of a biodegradable material or a combination of biodegradable materials. In another embodiment, the mold is composed of elastomeric or thermoplastic tubing. In another embodiment, the mold is composed of a glass. In another embodiment, the releasing agent is interposed between the mold and the solution. In another embodiment, the shell is cast.

In another embodiment, the stent devices as described herein provide adequate ventilation and drainage for normal middle ear function. In another embodiment, the stent devices as described herein restore ventilation and drainage for normal middle ear function. In another embodiment, the stent devices as described herein enhance ventilation and drainage for normal middle ear function. In another embodiment, the stent devices as described herein regulate ventilation and drainage for normal middle ear function. In another embodiment, the stent devices as described herein regulate air flow for normal middle ear function. In another embodiment, the stent devices as described herein regulate liquid flow for normal middle ear function. In another embodiment, the stent devices as described herein regulate pressure within the Eustachian tube for normal middle ear function. In another embodiment, a stent device confined to the Eustachian tube regulates pressure within the Eustachian tube for normal middle ear function. In another embodiment, the stent devices as described herein treat middle ear inflammation. In another embodiment, the stent devices as described herein treat reoccurring otitis media. In another embodiment, the stent devices as described herein treat chronic otitis media. In another embodiment, the stent devices as described herein treat dysfunctional ET. In another embodiment, the stent devices as described herein treat patulous ET. In another embodiment, the stent devices as described herein are drug eluting stent.

In another embodiment, the device is inserted for a long period of time. In another embodiment, the device remains in the isthmus for a long period of time. In another embodiment, the device remains in the isthmus for at least one year. In another embodiment, the device remains in the isthmus for at least two years. In another embodiment, the device remains in the isthmus for at least three years. In another embodiment, the device remains in the isthmus for at least four years. In another embodiment, the device remains in the isthmus for at least five years. In another embodiment, the device remains in the isthmus for at least seven years. In another embodiment, the device remains in the isthmus for at least ten years. In another embodiment, the device remains in the isthmus for at least sixteen years. In another embodiment, the device remains in the isthmus for at least twenty years.

In another embodiment, the device remains in the isthmus for at least one year. In another embodiment, the device remains in the isthmus for at least a month. In another embodiment, the device remains in the isthmus for at least three months. In another embodiment, the device remains in the isthmus for at least four months. In another embodiment, the device remains in the isthmus for at least five months. In another embodiment, the device remains in the isthmus for at least seven months.

In another embodiment, the device is inserted for a short period of time. In another embodiment, the device remains in the isthmus for no more than a year. In another embodiment, the device remains in the isthmus for no more than eight months. In another embodiment, the device remains in the isthmus for 2-8 weeks. In another embodiment, the device remains in the isthmus for 4-12 weeks. In another embodiment, the device remains in the isthmus for 10-35 weeks.

In another embodiment, the device is inserted into the Eustachian tube for a short period of time. In another embodiment, the device remains in the Eustachian tube for 2-8 weeks. In another embodiment, the device remains in the Eustachian tube for 6-12 weeks. In another embodiment, the device remains in the Eustachian tube for 1-3 months. In another embodiment, the device remains in the Eustachian tube for 2-6 months. In another embodiment, the device remains in the Eustachian tube for 4-12 months. In another embodiment, the device remains in the Eustachian tube for at least a year. In another embodiment, the device remains in the Eustachian tube for at least two years. In another embodiment, the device remains in the Eustachian tube for at least three years. In another embodiment, the device remains in the Eustachian tube for at least four years.

In another embodiment, the device is degraded at a programmed rate. In another embodiment, the device is designed to degrade at a rate wherein structure may be completely removed by aqueous solution flushing in twenty-four months, eighteen months, twelve months or the like. In another embodiment, the device maintains sufficient structural integrity to maintain patency of the Eustachian tube for a designed period of time. In another embodiment, the period of treatment may be for a period between two weeks, two months, six months, twelve months or more.

In another embodiment, a measure of the ability to maintain structural integrity would be that the stent can sustain a radially applied force without breaking (after the defined period of time) that is at least one-half of the structural force that can be sustained prior to implantation or immersion in a test environment. In another embodiment, the device comprises a lubricious, biologically neutral surface capable of eluting a surface-active agent, thereby mimicking the function of the normal Eustachian tube.

In another embodiment, it is well-known in the art that chemical materials, including lubricants, medicaments, and the like, may be dissolved or dispersed in a polymer and this will bloom or exude or migrate from the polymer for local delivery of the material.

In another embodiment, the device comprises an insertable member which comprises a shell. In another embodiment, the device comprises an insertable member which comprises an immobilizing means. In another embodiment, the insertable member provides sufficient air flow, gas flow, fluid flow, or any combination thereof. In another embodiment, the shell provides pressure control, sufficient air flow, gas flow, fluid flow, or any combination thereof.

In another embodiment, the device provides sufficient air communication between the ends of the Eustachian tube, gas communication between the ends of the Eustachian tube, fluid communication between the ends of the Eustachian tube, or any combination thereof In another embodiment, the device provides sufficient air communication between the middle ear and the nasopharynx (unidirectional). In another embodiment, the device provides unidirectional fluid communication and bidirectional air communication between the middle ear and the nasopharynx. In another embodiment, the device provides sufficient air communication between the proximal end and the distal end of the Eustachian tube, gas communication between the proximal end and the distal end of the Eustachian tube, fluid communication between the proximal end and the distal end of the Eustachian tube, or any combination thereof. In another embodiment, the shell provides sufficient air communication between the ends of the Eustachian tube, gas communication between the ends of the Eustachian tube, fluid communication between the ends of the Eustachian tube, or any combination thereof. In another embodiment, the shell provides sufficient air communication between the proximal end and the distal end of the Eustachian tube, gas communication between the proximal end and the distal end of the Eustachian tube, fluid communication between the proximal end and the distal end of the Eustachian tube, or any combination thereof.

In another embodiment, the device as described herein providing air communication between the ends of the Eustachian tube, gas communication between the ends of the Eustachian tube, fluid communication between the ends of the Eustachian tube, or any combination thereof is/are sufficient to effect pressure equilibration between the ends of the Eustachian tube. In another embodiment, the device as described herein providing air communication between the ends of the Eustachian tube, gas communication between the ends of the Eustachian tube, fluid communication between the ends of the Eustachian tube, or any combination thereof is/are sufficient to equilibrate the pressure between the ends of the Eustachian tube. In another embodiment, the device as described herein providing air communication between the ends of the isthmus tube, gas communication between the ends of the isthmus tube, fluid communication between the ends of the isthmus, or any combination thereof is/are sufficient to effect pressure equilibration between the ends of the isthmus. In another embodiment, the device as described herein providing air communication between the ends of the device, gas communication between the ends of the device, fluid communication between the ends of the device, or any combination thereof is/are sufficient to equilibrate the pressure between the ends of the Eustachian tube.

In another embodiment, the device as described herein providing air communication between the ends of the isthmus, gas communication between the ends of the isthmus tube, fluid communication between the ends of the isthmus, or any combination thereof is/are sufficient to effect pressure equilibration between the ends of the Eustachian tube.

In another embodiment, the construction of the device varies depending on the functionality desired. In another embodiment, the device is constructed according to the physiology of the subject into whose Eustachian tube is intended to receive. In another embodiment, a constructing factor is the specie of a subject. In another embodiment, a constructing factor is the age of a subject. In another embodiment, a constructing factor is the medical condition to be treated in a subject. In another embodiment, the subject is a human.

In another embodiment, the subject is an infant. In another embodiment, the subject is a child. In another embodiment, the subject is an adult. In another embodiment, the subject is a teenager. In another embodiment, the subject is a senior. In another embodiment, the subject is a mammal. In another embodiment, the subject is a pet. In another embodiment, the subject is a horse. In another embodiment, the subject is a farm animal. In another embodiment, the subject is a domesticated animal. In another embodiment, the subject is a non-domesticated animal. In another embodiment, the subject is any subject having an isthmus within a Eustachian tube.

In another embodiment, the device treats or prevents otitis media. In another embodiment, the device treats or prevents otitis media with effusion. In another embodiment, the device treats or prevents Eustachian tube dysfunction. In another embodiment, the device treats or prevents chronic retraction of the tympanic membrane. In another embodiment, the device treats or prevents chronic otitis media. In another embodiment, the device treats or prevents patulous ET.

In another embodiment, the device prevents narrowing of the isthmus. In another embodiment, the device prevents narrowing of the Eustachian tube. In another embodiment, the device prevents diseases associated with narrowing of the Eustachian tube. In another embodiment, the device prevents diseases associated with narrowing of the isthmus. In another embodiment, the device prevents medical conditions associated with narrowing of the isthmus. In another embodiment, the device is used for treating medical conditions associated with narrowing of the isthmus. In another embodiment, the device aerates the middle ear. In another embodiment, the device is a portal to drain fluid and infection from the middle ear. In another embodiment, the device treats retracted eardrums. In another embodiment, the device treats ear congestion. In another embodiment, the device prevents pressure related damage to the ear. In another embodiment, the device equilibrates pressure in the ear. In another embodiment, the device reduces high pressure in the ear. In another embodiment, the device increases low pressure in the ear. In another embodiment, the device equilibrates pressure in the ear associated with high altitude such as airplane travel. In another embodiment, the device equilibrates pressure in the ear associated with diving. In another embodiment, the device equilibrates pressure in the ear associated with over known altitude activities.

In another embodiment, the device enables the insertion of fiberoptic instruments through the isthmus. In another embodiment, the device enables diagnostic microendoscopy of Eustachian tube and the middle ear, and serve as a conduit for the diagnosis and assessment of middle and inner ear functions, integrity of the ossicles, chronic ear infection and cholesteatoma. In another embodiment, the device serves as a stent and protective dressing for the isthmus. In another embodiment, the device serves as a stern and protective dressing for the Eustachian tube.

In another embodiment, the device enables the insertion of fiberoptic instruments through the Eustachian tube. In another embodiment, the device enables diagnostic microendoscopy of Eustachian tube and the middle ear, and serve as a conduit for the diagnosis and assessment of middle and inner ear functions, integrity of the ossicles, chronic ear infection and cholesteatoma. In another embodiment, the device serves as a stent and protective dressing for the Eustachian tube.

In another embodiment, the device is constructed from biocompatible implantable material or materials. In another embodiment, the device comprises biomechanical properties that provide end forces necessary to keep the Eustachian tube orifice. In another embodiment, the device comprises biomechanical properties that provide end forces necessary to keep the isthmus orifice. In another embodiment, the device comprises a shell. In another embodiment, the shell is an insertable member.

Figure 2:
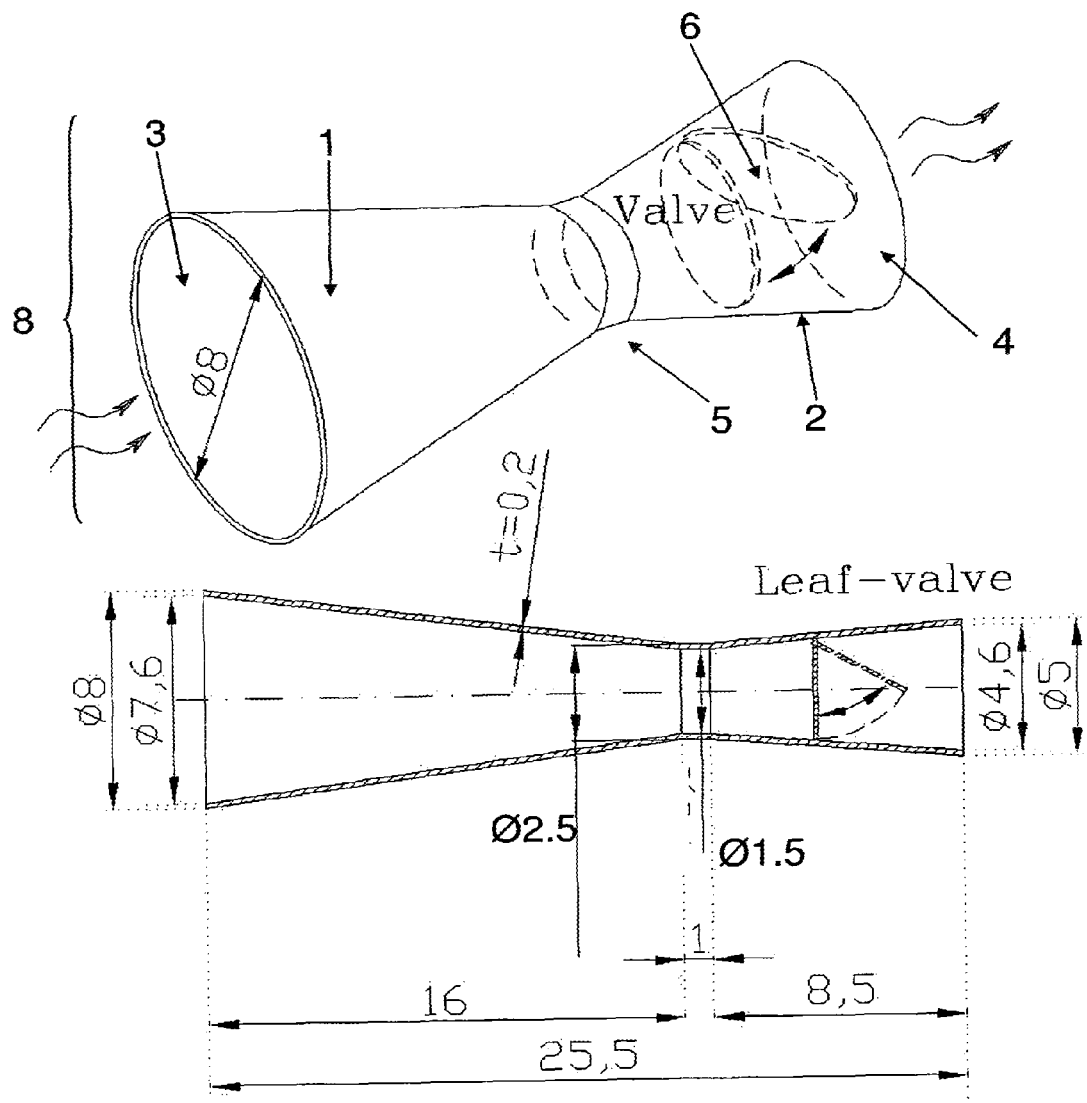
FIG. 2. is a schematic three dimensional drawing of the Stent (8) with a side view in accordance with an embodiment of the invention. The proximal cone (1) narrows from the proximal end (3) to the intermediate portion (5). The distal cone (2) widens towards the distal end (4). Disk shape, pressure actuated valve is located within the proximal cone (6).
Figure 3:
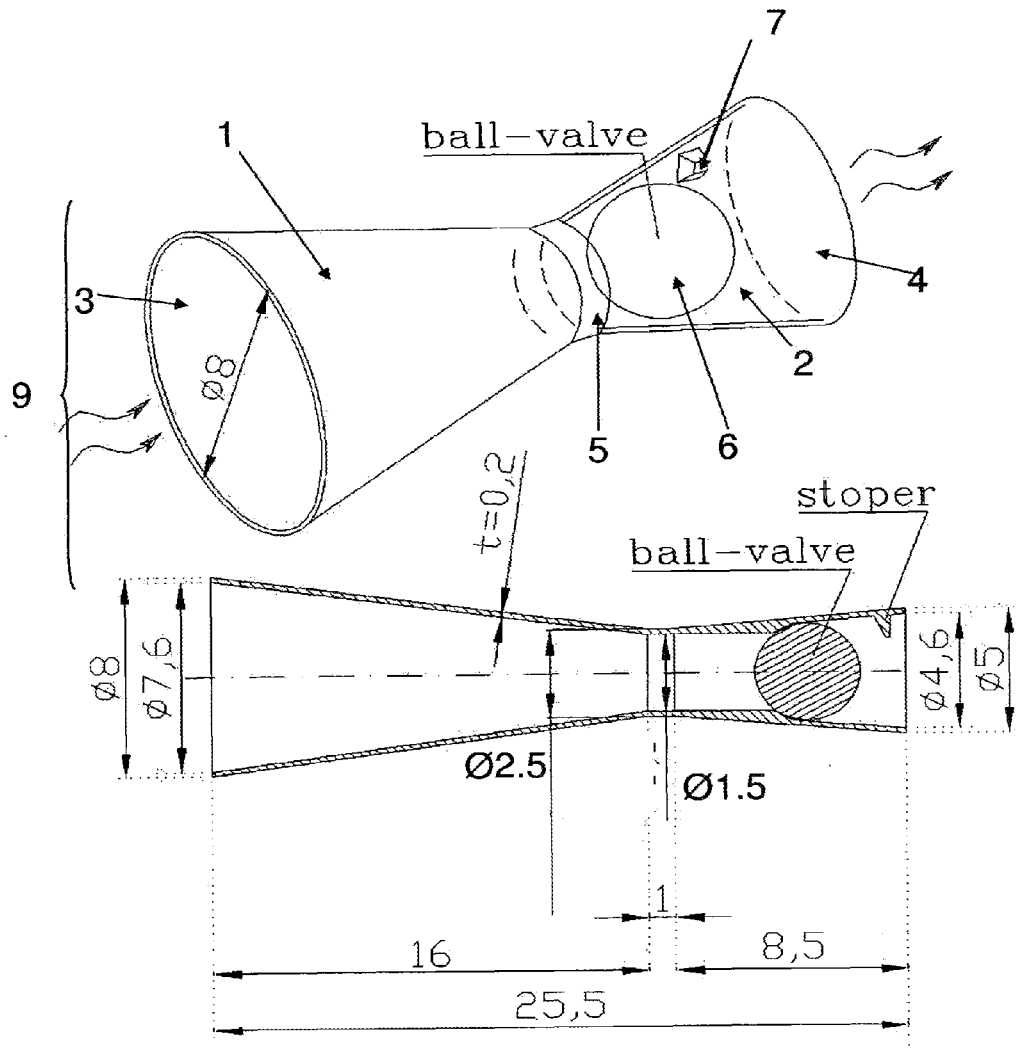
FIG. 3. is a schematic three dimensional drawing of the Stent (9) with a side view in accordance with an embodiment of the invention. The proximal cone (1) narrows from the proximal end (3) to the intermediate portion (5). The distal cone (2) widens towards the distal end (4). Ball shape, pressure actuated valve is located within the proximal cone (6). Also present on the proximal cone is an immobilizing means or anchoring means (7).

In another embodiment, the device comprises a shell (FIGS. 2 and 3) having a dual cone (1, 2), head to head shape with two ends (3, 4), the proximal end (3) and the distal end (4) and an intermediate portion (5). In another embodiment, the device comprises a coaxial shell having a dual cone, head to head shape with two ends, the proximal end resulting in an opening and the distal end resulting in an opening (FIGS. 2 and 3). In another embodiment, a device comprising a coaxial shell having a dual cone, head to head shape with two ends, the proximal end and the distal end also comprises a valve (6). In another embodiment, a device comprising a coaxial shell having a dual cone, head to head shape with two ends, the proximal end and the distal end also comprises a pressure biasing valve. In another embodiment, a device comprising a coaxial shell having a dual cone, head to head shape with two ends, the proximal end and the distal end also comprises a valve for equilibrating pressure between the proximal and distal ends of the shell. In another embodiment, a device comprising a coaxial shell having a dual cone, head to head shape with two ends, the proximal end and the distal end also comprises a pressure actuated valve (6). In another embodiment, a device comprising a coaxial shell having a dual cone, head to head shape with two ends and an immobilizing means (stopper (7)). In another embodiment, a device comprising a coaxial shell having a dual cone, head to head shape with two ends, the proximal end and the distal end also comprises a pressure actuated valve (6) and an immobilizing means (stopper (7)) (FIG. 3).

In another embodiment, the pressure actuated valve blocks air flow through the Eustachian tube. In another embodiment, the pressure actuated valve blocks fluid flow through the Eustachian tube. In another embodiment, the pressure actuated valve blocks gas flow through the Eustachian tube. In another embodiment, the pressure actuated valve is a rotating disc. In another embodiment, the pressure actuated valve has a ball shape. In another embodiment, pressure actuated valves are known to one of ordinary skill in the art.

In another embodiment, the pressure actuated valve blocks air flow through the isthmus. In another embodiment, the pressure actuated valve blocks fluid flow through the isthmus. In another embodiment, the pressure actuated valve blocks gas flow through the isthmus. In another embodiment, the pressure actuated valve is a rotating disc. In another embodiment, the pressure actuated valve has a ball shape. In another embodiment, pressure actuated valves are known to one of ordinary skill in the art. In another embodiment, pressure actuated valves are flower shaped wherein the leaves of the flower are wide in the periphery and narrow in the center. In another embodiment, pressure actuated valves pivot thus creating horizontal axis rotation in response to pressure changes. In another embodiment, pressure actuated valves are known to one of average skill in the art. In another embodiment, pressure actuated valves comprise two cones which move forward as response to pressure thus creating a seal.

In another embodiment, the valve is in a close position in steady state. In another embodiment, pressure exerted from the proximal end of the device actuates the valve, thus opening it. In another embodiment, pressure exerted from the distal end of the device actuates the valve, thus opening it.

In another embodiment, the pressure actuated valve opens upon exerting a pressure of above 20 mmHg between the proximal and the distal ends (either way). In another embodiment, the pressure actuated valve opens upon exerting a pressure of above 30 mmHg between the proximal and the distal ends (either way). In another embodiment, the pressure actuated valve opens upon exerting a pressure of above 40 mmHg between the proximal and the distal ends (either way). In another embodiment, the pressure actuated valve opens upon exerting a pressure of above 50 mmHg between the proximal and the distal ends (either way).

In another embodiment, the pressure actuated valve opens upon exerting a pressure of above 50 mmH2O between the proximal and the distal ends (either way). In another embodiment, the pressure actuated valve opens upon exerting a pressure of above 70 mmH2O between the proximal and the distal ends (either way). In another embodiment, the pressure actuated valve opens upon exerting a pressure of above 80 mmH2O between the proximal and the distal ends (either way). In another embodiment, the pressure actuated valve opens upon exerting a pressure of above 90 mmH2O between the proximal and the distal ends (either way). In another embodiment, the pressure actuated valve opens upon exerting a pressure of above 100 mmH2O between the proximal and the distal ends (either way). In another embodiment, the pressure actuated valve opens upon exerting a pressure of above 110 mmH2O between the proximal and the distal ends (either way). In another embodiment, the pressure actuated valve opens upon exerting a pressure of above 120 mmH2O between the proximal and the distal ends (either way). In another embodiment, the pressure actuated valve opens upon exerting a pressure of above 130 mmH2O between the proximal and the distal ends (either way). In another embodiment, the pressure actuated valve opens upon exerting a pressure of above 140 mmH2O between proximal and the distal ends (either way). In another embodiment, the pressure actuated valve opens upon exerting a pressure of above 150 mmH2O between the proximal and the distal ends (either way). In another embodiment, the pressure actuated valve opens upon exerting a pressure of above 175 mmH2O between the proximal and the distal ends (either way). In another embodiment, the pressure actuated valve opens upon exerting a pressure of above 200 mmH2O between the proximal and the distal ends (either way).

In another embodiment, the device comprises a shell having a dual funnel, nozzle to nozzle shape with two ends. In another embodiment, the funnel's arch dimensions vary in order to fit a particular anatomy and/or promote immobilization of the device. In another embodiment, the device comprises a shell having a shape generally corresponding to dual acute isosceles head to head shape. In another embodiment, the device comprises a shell having a shape generally corresponding to dual isosceles head to head shape. In another embodiment, the shape of the device corresponds to the cross sectional area of the Eustachian tube, torus tubarius, isthmus, or any combination thereof.

In another embodiment, the dimensions of the device: (1) promote insertion through the isthmus; and (2) promote immobilization of the device thus anchoring it to the isthmus. In another embodiment, the immobilization means (7) promote immobilization of the device. In another embodiment, the immobilization means anchor the device to the isthmus. In another embodiment, the dimensions of the device: promote insertion through the Eustachian tube; and promote immobilization of the device thus anchoring it to the Eustachian tube. In another embodiment, the immobilization means (7) promote immobilization of the device. In another embodiment, the immobilization means anchor the device to the isthmus. In another embodiment, the immobilization means anchor the device to a specific location within the Eustachian tube. In another embodiment, the immobilization means anchor the device to a specific location within the isthmus. In another embodiment, the immobilization means anchor the device to a specific location within the proximal portion of the ET. In another embodiment, the device is a tube comprising different portions wherein each portion has a different diameter. In another embodiment, the device is a tube which widens towards its ends. In another embodiment, the device is a tube which widens from the intermediate portion towards its ends. In another embodiment, an intermediate portion is uniform with regard to its diameter. In another embodiment, an intermediate portion is uniform. In another embodiment, the intermediate portion is the narrowest portion of the device. In another embodiment, the intermediate portion (5) is designed to fit within the isthmus. In another embodiment, the proximal and distal ends (3, 4) protrude out of the isthmus and to the Eustachian tube. In another embodiment, the proximal and distal ends protrude out of the isthmus and to the Eustachian tube thus anchoring the device comprising a shell to the isthmus. In another embodiment, the proximal and distal ends protrude out of the isthmus and to the Eustachian tube thus contributing to the immobilization of the device comprising a shell. In another embodiment, the proximal and distal ends are elastic and thus the insertion of the device into the isthmus is enabled. In another embodiment, the device is designed to occupy only the proximal portion of the ET and thus comprises a cone shape, a funnel shape or a triangular shape which fits between the proximal end of the isthmus or 0.1-5 mm proximal to the proximal end of the isthmus and towards the proximal end of the ET.

In another embodiment the proximal portion of the ET is the cartilaginous portion of the ET. In another embodiment the distal portion of the ET is the osseous of the ET.

In another embodiment, the narrowest portion of the Eustachian tube is the isthmus, which ranges in dimension from 2 to 3 mm vertically and 1 to 1.5 mm horizontally. In another embodiment, the diameter of any cross-section within the intermediate portion does not exceed 5 mm. In another embodiment, the diameter of any cross-section within the intermediate portion does not exceed 4.5 mm. In another embodiment, the diameter of any cross-section within the intermediate portion does not exceed 4 mm. In another embodiment, the diameter of any cross-section within the intermediate portion does not exceed 3.5 mm. In another embodiment, the diameter of any cross-section within the intermediate portion does not exceed 3 mm. In another embodiment, the diameter of any cross-section within the intermediate portion does not exceed 2 mm. In another embodiment, the diameter of any cross-section within the intermediate portion does not exceed 1.5 mm. In another embodiment, the diameter of any cross-section within the intermediate portion does not exceed 1 mm. In another embodiment, the length of the intermediate portion is 1-6 mm. In another embodiment, the length of the intermediate portion is 1-5 mm. In another embodiment, the length of the intermediate portion is 2-5 mm. In another embodiment, the length of the intermediate portion is 2-4 mm. In another embodiment, the length of the intermediate portion is 2-3 mm.

In another embodiment, the diameter of the proximal end is larger than 3 mm. In another embodiment, the diameter of the proximal end is larger than 3.5 mm. In another embodiment, the diameter of the proximal end is larger than 4 mm. In another embodiment, the diameter of the proximal end is larger than 4.5 mm. In another embodiment, the diameter of the proximal end is larger than 5 mm. In another embodiment, the diameter of the proximal end is larger than 5.5 mm. In another embodiment, the diameter of the proximal end is larger than 6 mm. In another embodiment, the diameter of the proximal end is larger than 6.5 mm. In another embodiment, the diameter of the proximal end is larger than 7 mm. In another embodiment, the diameter of the proximal end is larger than 8 mm.

In another embodiment, the device dilates the Eustachian tube. In another embodiment, the device dilates and stents the Eustachian tube. In another embodiment, the device stents the isthmus. In another embodiment, the device ventilates the middle ear.

In another embodiment, the device comprises a structural memory to maintain its shape. In another embodiment, the device comprises a shell having opposing ends or ends (3, 4). In another embodiment, the device is formed at least in part from a biocompatible material.

In another embodiment, the opposing ends are connected by a peripheral surface. In another embodiment, at least one exterior surface have a shape that substantially corresponds to a cross sectional area of the Eustachian tube. In another embodiment, at least one exterior surface have a shape that substantially corresponds to a cross sectional area of the isthmus. In another may have any desired contour, e.g., jagged, undulated, etc.

In another embodiment, the length of the device is greater than the width of the device. In another embodiment, the length of the device extends the width by at least 100%. In another embodiment, the length of the device extends the width by at least 200%. In another embodiment, the length of the device extends the width by at least 300%. In another embodiment, the length of the device extends the width by at least 400%. In another embodiment, the device is constructed for insertion into the isthmus in an ear, left or right, the device may have a member geometry that exhibits minor symmetry. In another embodiment, the device is constructed for insertion into the Eustachian tube in an ear, left or right, the device may have a member geometry that exhibits mirror symmetry.

In another embodiment, the shell and the immobilization means (7) have an integrated construction. In another embodiment, the device have mechanical properties that provide forces necessary to render the device immobile, e.g., the member may be at least partially elastically deformable before immobilization. In another embodiment, the device itself is formed from a material compounded with one or more adhesives. In another embodiment, an adhesive is applied as an interfacial composition between the shell and the isthmus. In another embodiment, an adhesive is applied as an interfacial composition between the shell and the Eustachian tube.

In another embodiment, the device has dimensions that are designed to provide a slit between the shell's exterior surface and the isthmus. In another embodiment, the device has dimensions that are designed to provide a slit between the shell's exterior surface and the Eustachian tube. In another embodiment, the surface of the device is not in full contact with the isthmus. In another embodiment, the surface of the device is not in full contact with the Eustachian tube. In another embodiment, the device is in contact with the Eustachian tube at predefined locations. In another embodiment, these predefined locations serve as immobilizing means. In another embodiment, these predefined locations serve as posterior or anterior pillars.

In another embodiment, the device is effective in equilibrating any fluid-generated pressure between the proximal and distal ends of the device. In another embodiment, the device is effective in equilibrating any gas-generated pressure between the proximal and distal ends of the device.

In another embodiment, the invention pertains to a method for inserting a device into a Eustachian tube in a subject providing pressure controlled ventilation, and enhanced drainage, or a combination thereof to a middle ear of a subject, comprising a shell, wherein the shell comprises a proximal end, a distal end, wherein the device occupies at least a portion of the proximal end of the Eustachian tube of a subject. In another embodiment, the device of occupis only the Eustachian tube. In another embodiment, the proximal end cross-section area is larger than the distal end cross-section area. In another embodiment, the device further comprises an intermediate portion. In another embodiment, the proximal end and the distal end have a larger cross-section area than the intermediate portion cross-section area, wherein the intermediate portion fits within the Eustachian tube in a subject In another embodiment, the invention pertains to a method for insertion a device into a Eustachian tube in a subject providing pressure controlled ventilation, and enhanced drainage, or a combination thereof to a middle ear of a subject, comprising a shell, wherein the shell comprises a proximal end, a distal end, and an intermediate portion, wherein the proximal end and the distal end have a larger cross-section area than the intermediate portion cross-section area, wherein the intermediate portion fits within the Eustachian tube in a subject. In another embodiment, the device is inserted through the nasopharynx into the isthmus.

In another embodiment, the invention pertains to a method for inserting a device of the invention as described herein into a Eustachian tube in a subject. In another embodiment, the invention pertains to a method for inserting a device of the invention as described herein through the isthmus providing pressure control ventilation, and enhanced ventilation, drainage, or a combination thereof to a middle ear of a subject.

In another embodiment, the invention pertains to a method for stenting the Eustachian tube with a device as described herein, providing pressure controlled ventilation or enhanced drainage, or a combination thereof to a middle ear of a subject.

In another embodiment, the invention pertains to a method for inserting a device through the isthmus and into a Eustachian tube of a subject. In another embodiment, the device is used to dilate the Eustachian tube at the isthmus. In another embodiment, the device is used to provide mechanical support to the Eustachian tube. In another embodiment, the device is used to provide mechanical support to isthmus. In another embodiment, the device is used to stent the Eustachian tube at the isthmus. In another embodiment, the device is used to stent the isthmus.

In another embodiment, the invention pertains to a method for inserting the device as described herein into an Eustachian tube and through the isthmus of a subject, comprising: (a) loading the device onto an insertion apparatus, wherein the device comprises a coaxial shell, wherein the shell comprises a proximal end, a distal end, and an intermediate portion, wherein the proximal end and the distal end have a larger cross-section area than the intermediate portion cross-section area, wherein the intermediate portion fits within an isthmus in the Eustachian tube in a subject; (b) inserting the device using the insertion apparatus through a nostril or mouth of a subject into the isthmus; and (c) releasing the device from the apparatus in an isthmus.

In another embodiment, the invention provides a method for inserting a device into a Eustachian tube of an animal. The method involves inserting the device as described above through a nostril or mouth of the animal into the Eustachian tube. Optionally, the device is inserted solely through the nasopharyngeal end of the Eustachian tube through the nose or the oropharynx in a manner that does not involve making any incision to an eardrum or ear canal skin. The device may then be released manner effective to allow the device to immobilize itself within the Eustachian tube at its end in the nasopharynx. The method may be performed with general anesthesia, local anesthesia, or sedation as appropriate.

In another embodiment, the method of placement of the device is via the nasal passageways and nasopharyngeal end of the Eustachian tube and does not require incision of the eardrum, ear canal or entry into the middle ear. In another embodiment, the method of placement of the device is via the oral passageways and nasopharyngeal end of the Eustachian tube and does not require incision of the eardrum, ear canal or entry into the middle ear.

In another embodiment, the method comprises loading the device onto an insertion apparatus and using the insertion apparatus to insert the device through a nostril or mouth of a subject into the isthmus. In another embodiment, the method comprises loading the device onto an insertion apparatus and using the insertion apparatus to insert the device through a nostril or mouth of a subject through the Eustachian and into the isthmus. In another embodiment, once the device is in place, the device is released from the apparatus in a manner effective to allow the device to immobilize itself within the isthmus.

In another embodiment, the method comprises endoscopy, in conjunction with surgery or in the absence of any incision. In another embodiment, the method is effective to dilate the Eustachian tube. In another embodiment, the method is effective to permanently In another embodiment, the method is effective to prevent collapse of the Eustachian tube.

In another embodiment, the device is effective in treating certain types of hearing loss. In another embodiment, the device is effective in treating ear discomfort. In another embodiment, the device is effective in treating dysfunction of the Eustachian tube. In another embodiment, the device is effective in treating inflammation affecting the Eustachian tube. In another embodiment, the device enables diagnostic microendoscopy of Eustachian tube and the middle ear, and serves as a conduit for the diagnosis and assessment of middle and inner ear functions, integrity of the ossicles, chronic ear infection and cholesteatoma. In another embodiment, the device serves as a stent and protective dressing for any hard and soft palate, nasopharyngeal, or Eustachian tube surgery.

In another embodiment, the device is effective in treating retracted eardrums and ear congestion. In another embodiment, by dilating and stenting the Eustachian tube, barometric Eustachian tube dysfunction is treated, and pressure related damage to the ear are prevented. In another embodiment, allergic and/or infectious Eustachian tube dysfunction is treated by the device. In another embodiment, chronic and acute Eustachian tube dysfunction is treated by the device.

In another embodiment, when placed in the isthmus at the Eustachian tube through a minimally invasive procedure that results in device placement through the nasal passages through the nasopharynx or the oropharynx, the device confers a number of advantages. In another embodiment, the benefits of a nasopharyngeal-based therapy are achieved without the disadvantages of the undesirable outcomes associated with treatment methods that involve an incision in the ear canal or eardrum, or entry into the middle ear space. In another embodiment, such placement of the device in the ET provides immediate relief from fluid in the ear and pressure related maladies.

In another embodiment, the insertion apparatus is used to place the device into the isthmus within the Eustachian tube. In another embodiment, the insertion apparatus may have a number of designs and construction. In another embodiment, the insertion apparatus is endoscopic and hand held in construction. In another embodiment, the apparatus provides a user sufficient degree of control over the insertion of the device in a minimally invasive manner so as to minimize trauma or discomfort to a patient. In another embodiment, the apparatus provides for precisely and accurately controlled translational (e.g., X-Y-Z) and/or, rotational (.theta.-.phi.) movement capabilities. In another embodiment, the apparatus allows for one, two, three, four, five, six, or more degrees of freedom.

In another embodiment, the apparatus have a device-interfacing terminus and a manipulation terminus. In another embodiment, the device-interfacing terminus have a construction specific to the device or is used to interface with devices other than those described herein. In another embodiment, the interfacing terminus has a solid or hollow geometry specific to the device. In another embodiment, the interfacing terminus provides for functionality associated with the practice of the method.

In another embodiment, the manipulation terminus houses a means for releasing any device engaged therewith. In another embodiment, the releasing means has a spring-loaded mechanism, or manual release mechanism that allows the device to be releasably engageable with device-interfacing terminus of the apparatus. In another embodiment, the device is controllably slid from the insertion apparatus into the Eustachian tube.

In another embodiment, the device is constructed with a means for interfacing with the insertion apparatus. In another embodiment, such means serve no other purpose than to interface with the insertion apparatus. For example, the interfacing means may include at least one protrusion extending from an exterior surface by which the insertion device may grab. As another example, one or more tabs or fenestrations may be located on other or both front and back surfaces of the device around the fluid-communication providing means.

In another embodiment, the interfacing means serves a plurality of purposes. In another embodiment, the shell is effective to serve as means for engaging with the insertion apparatus.

In another embodiment, the interfacing means is used to make adjustments to the device to be inserted and/or extracted. In another embodiment, the interfacing means is used to adjust the shell size before insertion. In another embodiment, the interfacing means is used to stretch the shell before insertion. In another embodiment, the interfacing means is used to squeeze the shell before insertion.

In another embodiment, the device is packaged with the insertion apparatus to form a kit. In another embodiment, the kit comprises instruction for using the apparatus with the device. In another embodiment, the kit keeps the device sterile. In another embodiment, the kit keeps the insertion apparatus sterile. In another embodiment, the kit keeps the device and the insertion apparatus sterile. In another embodiment, the kit keeps the device and the insertion apparatus in minimized dimensions.

EXPERIMENTAL DETAILS SECTION

Insertion Procedure

Device 8 or 9 (FIGS. 2 and 3) is inserted through the nasopharyngeal orifice as described below, such that surgery and lifting of the tympanic membrane is not required.

The patient is placed in a supine position on the operating table under either general or local anesthesia. Ephedrine is administered intranasally.

The nose is inspected using a 2.4-4 mm or narrower flexible or rigid endoscope fitted with a video camera processor and a light source, attached to a guide with a Stent placed on it. After reaching the nasopharynx, the Eustachian tube orifice is identified, and then using angulations of the endoscope and the guide, it is inserted and placed. Once the Stent is in place, a catheter is used to conduct suction of the middle ear. Finally, the endoscope is removed from the nasal cavity. In some cases a inflation of the tube by air will done before inserting the stent.

Turning now to FIGS. 1-3, it is to be understood that such figures show specific examples of the devices and methods of the present invention. Any elements, attributes, components, accessories or features of one embodiment or example shown in these figures may be eliminated from that embodiment or example, or may be included in any other embodiment or example, unless to do so would render the resultant embodiment or example unusable for its intended purpose.

FIG. 1 generally shows a diagram of the inner ear of a human patient wherein device 8 is being implanted in the Eustachian tube. As shown, device 8 comprises a valve 6 and a narrow intermediate portion 5 that fits and or fastens device 8 to the isthmus within the Eustachian tube. Valve 6 is an open position due to elevated pressure, allowing air and fluid communication between the proximal (3) and distal (4) ends of the device 8.

Prior to or after insertion of the device, the implantable device is loaded onto the insertion apparatus into the lumen of Eustachian tube in a parallel position to the Eustachian tube and the isthmus, thus providing mechanical support to the isthmus. The structure and dimensions of the shell of device 8 allow contact between the shell and: (a) the isthmus (intermediate portion 5) and (b) the Eustachian tube (proximal and distal portions), in some discrete portions, but still allow sub-millimeter spaces in other discrete locations of the shell, in-between the shell and the underlying tissue. In a case that such compression for deployment is not possible, the size of the narrowest part and the distal part will be the same and a wider stopper will be placed inside the lumen of the stent to prevent re-compression and migration.

FIG. 2 is a side view of the device with an optional leaf valve positioned in the distal side in accordance with an embodiment of the invention. The exact measurements of the stent are calculated according to age and size of the Eustachian tube. Thus, the Stent may assume or be provided in several sizes. In this example, the Stent's proximal inner diameter is 7.6 mm and outer diameter 8.0 mm. The Stent's distal inner diameter is 4.6 mm and outer diameter 5 mm. The inner diameter at the narrowest part is about 1-1.5 mm and outer diameter 3.5 mm. The proximal length is 16 mm (or less) and the distal length 8.5 mm (or less). The narrowest part's length is 1 mm. Other dimensions are possible. The valve is placed in the distal side and it might be one directional or two directional as needed. There is also possibility of positioning the valve in the proximal part or not to put a valve at all. The shape, texture and finish of the device wall vary, such as for example spiral, network or a smooth texture depending on the material chosen, drainage needs or other consideration.

FIG. 3—is similar to FIG. 2, but the valve is in a ball shape, and it includes a stopper that assists to prevent the migration of the device within the Eustachian tube and out of the isthmus. The stopper may also prevent a compression of the deployed stent that could allow the stent to migrate back through the isthmus. Other known means of preventing collapse of the device can be deployed by one of average skill in the art.

What is claimed:

1. A method of treating a patient having at least one of otitus media with effusion, recurrent otitus media, chronic otitus media, Eustachian tube disfunction, patulous ET, chronic retraction of a tympanic membrane, ear congestion and ear infection, comprising:

obtaining a device adapted for insertion into a Eustachian tube, said device comprising a shell, said shell comprising a proximal end, a distal end, and a tube extending from the proximal end to the distal end, the tube being closed in a resting position, and opened by air pressure differential between the ends when air pressure exerted at the proximal end is higher than air pressure exerted at the distal end and when air pressure exerted at the distal end is higher than air pressure exerted at the proximal end, and wherein the device is adapted for insertion into the Eustachian tube through a nasopharynx;

inserting the device into a Eustachian tube of the patient through a nasopharynx of the patient; and immobilizing the device in the Eustachian tube.

2. The method of claim 1, wherein said inserting comprises:

loading the device onto an insertion apparatus;

inserting the device using the insertion apparatus into the Eustachian tube through the nasopharynx; and releasing the device from the apparatus upon device insertion into the Eustachian tube.

3. The method of claim 1, further comprising fitting an intermediate portion of the device within an isthmus of the patient.

4. The method of claim 3, further comprising compressing at least a portion of the device to fit within the isthmus.

5. The method of claim 1, wherein said inserting is through a nostril of the patient.

6. The method of claim 1, wherein the tube is opened by opening a pressure actuated artificial valve situated between the proximal end and the distal end to equalize the air pressure differential between the distal end and the proximal end.

7. The method of claim 1, wherein said inserting comprises locating the device wholly within a cartilaginous portion of the Eustachian tube.

8. The method of claim 1, further comprising releasing a pharmacologically active agent from the device.

9. The method of claim 1, further comprising adapting the tube to open only upon occurrence of an air pressure differential of above 200 mmH$_2$O between the proximal end and the distal end.

10. The method of claim 1, further comprising fitting at least a part of the device within a part of a cartilaginous portion of the Eustachian tube.

* * * * *